(12) United States Patent
Kobayashi

(10) Patent No.: US 7,165,452 B2
(45) Date of Patent: Jan. 23, 2007

(54) MEASURING METHOD, MEASUREMENT-SIGNAL OUTPUT CIRCUIT, AND MEASURING APPARATUS

(75) Inventor: Yoshihiro Kobayashi, Komogane (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 10/800,130

(22) Filed: Mar. 12, 2004

(65) Prior Publication Data
US 2005/0081635 A1   Apr. 21, 2005

(30) Foreign Application Priority Data
Mar. 14, 2003   (JP) .............................. 2003-069741

(51) Int. Cl.
*G01H 13/00*   (2006.01)
(52) U.S. Cl. ........................ 73/580; 73/61.75
(58) Field of Classification Search .................. 73/580
See application file for complete search history.

(56) References Cited

U.S. PATENT DOCUMENTS

| | | | |
|---|---|---|---|
| 3,953,844 A | | 4/1976 | Barr et al. |
| 4,618,014 A | | 10/1986 | Kobayashi |
| 5,705,399 A | * | 1/1998 | Larue .......................... 73/580 |
| 6,041,642 A | * | 3/2000 | Duncan ..................... 73/24.01 |
| 6,557,416 B2 | * | 5/2003 | Chang et al. ................. 73/579 |
| 6,722,200 B2 | * | 4/2004 | Roukes et al. ............... 73/580 |
| 6,756,793 B2 | * | 6/2004 | Hirono et al. ............ 73/335.04 |
| 2003/0033876 A1 | | 2/2003 | Roukes et al. | |

FOREIGN PATENT DOCUMENTS

| | | |
|---|---|---|
| JP | 6-308009 | 11/1994 |
| JP | 07-043284 | 2/1995 |
| JP | 8-29218 | 2/1996 |
| JP | 10-065525 | 3/1998 |
| JP | 2002-39934 | 2/2002 |

OTHER PUBLICATIONS

Horowitz et al., The Art of Electronics, Cambridge University Press, Cambridge, 1980, p. 436.*
Bruschi et al, "Inexpensive but accurate driving circuits for quartz crystal microbalances", Review of Scientific Instruments, American Institute of Physics, US, vol. 70, No. 1, Jan. 1999, pp. 153-157.
Patent Abstracts of Japan re: Publication No. 07043284, Feb. 14, 1995.
Communication from European Patent Office re: related application, May 18, 2006.

* cited by examiner

*Primary Examiner*—John E. Chapman
(74) *Attorney, Agent, or Firm*—Harness, Dickey & Pierce, P.L.C.

(57) ABSTRACT

A measuring apparatus for detecting a change in frequency of a piezoelectric vibrating reed is realized with a simple circuit. The circuit of the measuring apparatus includes a phase lock loop circuit 20 which includes a phase comparator 22, a loop filter 24, and a voltage-controlled oscillator 26. An oscillator circuit 10 of a piezoelectric vibrating reed 12 is connected to the phase comparator 22. An output terminal 30 is provided downstream of the loop filter 24. In a method for measuring mass from a change in oscillation frequency of the piezoelectric vibrating reed 12, an input signal from the piezoelectric vibrating reed 12 is input to the phase comparator 22 of the phase lock loop circuit 20 and the oscillation frequency of the piezoelectric vibrating reed 12 is obtained based on the output from the loop filter 24 of the phase lock loop circuit 20.

7 Claims, 4 Drawing Sheets

MEASURING METHOD, MEASUREMENT-SIGNAL OUTPUT CIRCUIT, AND MEASURING APPARATUS

FIELD OF THE INVENTION

The present invention relates to a measuring method, a measurement-signal output circuit, and a measuring apparatus. In particular, the present invention relates to a measuring method, a measurement-signal output circuit, and a measuring apparatus suitable for the detection of a change in frequency due to a slight adhesion in mass on a piezoelectric vibrating reed functioning as a measuring sensor.

DESCRIPTION OF THE BACKGROUND ART

In the fields of, for example, food, biochemistry, and the environment, the Quartz Crystal Microbalance (hereinafter, referred to as QCM) method is used to measure, for example, presence of a specific substance and the density of such a substance. This QCM method employs a mass-measuring quartz vibrator which includes, as a major component, a quartz vibrating reed as a piezoelectric vibrating reed provided with a sensitive membrane which absorbs a specific substance. The sensitive membrane of the mass-measuring quartz vibrator has a molecular recognition function for achieving, for example, the densitometry and detection of the specific substance, and an exciting electrode is formed on the piezoelectric vibrating reed (quartz vibrating reed). For example, the detection and densitometry of a specific substance in liquid by the QCM method is carried out as follows.

A piezoelectric vibrating reed having a sensitive membrane formed thereon is placed in a solution and then oscillated until the oscillation frequency in this liquid stabilizes. Then, a substance which causes the reaction of absorbing or depositing substances in the liquid onto the sensitive membrane or the reaction of desorbing or decomposing substances on the sensitive membrane or a substance to be detected is added to the liquid, and the sensitive membrane on the piezoelectric vibrating reed is reacted with the specific substance to be measured. As a result, the mass on an exciting electrode of the piezoelectric vibrating reed increases or decreases, and the oscillation frequency of the piezoelectric vibrating reed decreases or increases accordingly. Consequently, the presence, density, and mass of the specific substance to be measured in the liquid can be obtained.

Japanese Unexamined Patent Application Publication No. 7-43284 describes an assay system for the amount of chemical substance by this QCM method.

In this method, a piezoelectric vibrating reed having a sensitive membrane formed thereon is connected to an oscillator circuit. This oscillator circuit is connected to a frequency counter. Furthermore, this frequency counter is connected to a computer. In an apparatus with the above-described structure, the piezoelectric vibrating reed is placed in a solution containing chemical substances and then oscillated. The oscillation frequency at this time is measured with the frequency counter. A change in frequency is obtained by subtracting from this measured oscillation frequency the frequency when the above-described sensor placed in a solution not containing chemical substances is oscillated, so that quantitative analysis of the chemical substances is performed.

In the conventional measuring apparatus with the above-described structure, the oscillation frequency of the piezoelectric vibrating reed is measured with a frequency counter, which separately requires a highly stable frequency oscillator source, and the frequency accuracy greatly affects the measurement accuracy. Furthermore, a highly stable and accurate frequency counter is expensive, and the conventional measuring apparatus is large.

In addition, measurement with a frequency counter requires at least one second of measuring time to increase the measurement accuracy, which is too long to detect a change in frequency in a short period of time.

Also, an oscillator circuit has temperature characteristics, and hence a change in temperature in the measurement environment greatly affects the measurement accuracy. In order to eliminate measurement errors associated with temperature characteristics, the system of measurement needs to be installed in a temperature-controlled environment, which causes the measuring system to become costly and large.

To overcome the drawbacks associated with the known art, an object of the present invention is to construct a measuring apparatus for detecting a change in frequency of a piezoelectric vibrating reed with a simple circuit and to provide a measuring method and a measuring apparatus for a mass-measuring vibrating reed which makes this measuring apparatus inexpensive and compact.

SUMMARY OF THE INVENTION

In order to achieve the above-described object, a measuring method, a measurement-signal output circuit, and a measuring apparatus according to the present invention have the following features. In a method for measuring the mass of a substance to be detected which adhered to the piezoelectric vibrating reed based on a change in oscillation frequency of a mass-measuring piezoelectric vibrating reed, the change resulting from the substance sticking to the piezoelectric vibrating reed, the oscillation frequency of the piezoelectric vibrating reed is input to a phase comparator of a phase lock loop circuit as an input signal. In the phase lock loop circuit, the oscillation frequency of the piezoelectric vibrating reed is obtained based on the output from a loop filter connected downstream of the phase comparator.

With this structure, the phase lock loop (PLL) circuit is controlled so as to phase-synchronize with the oscillation frequency of the piezoelectric vibrating reed. Thus, the output from the loop filter constituting the PLL circuit correlates with the oscillation frequency of the above-described piezoelectric vibrating reed. That is, when the oscillation frequency of the above-described piezoelectric vibrating reed changes, the output from the loop filter also changes according to the change in the above-described oscillation frequency. A change in oscillation frequency of the above-described piezoelectric vibrating reed can be obtained by measuring the amount of change in output from the loop filter.

This is a measurement-signal output circuit for outputting a signal for detecting the oscillation frequency of an oscillator circuit which oscillates a mass-measuring piezoelectric vibrating reed. The measurement-signal output circuit includes a voltage-controlled oscillator oscillatable at an oscillation frequency of the piezoelectric vibrating reed; a phase detector which obtains the difference in phase between an output signal from the voltage-controlled oscillator and an output signal from the oscillator circuit; and a loop filter having an output end connected to the voltage-controlled oscillator and an output terminal and outputting a voltage according to the difference in phase obtained by the phase detector.

In this case, the above-described piezoelectric vibrating reed includes a sensitive membrane on an exciting electrode on one surface thereof so that it is used for measurement in liquid. Furthermore, the above-described piezoelectric vibrating reed includes a sensitive membrane on an exciting electrode on one surface thereof or sensitive membranes on the exciting electrodes on both surfaces thereof so that it is used for measurement in air. In addition, a measuring apparatus including these measurement-signal output circuits can be constructed.

With this structure, the voltage-controlled oscillator, the phase detector, and the loop filter constitute a PLL circuit and an output terminal is provided at the output end of the above-described loop filter. Hence, a part of the voltage output from the loop filter that controls the oscillation frequency of the oscillator circuit so that the oscillation frequency phase-synchronizes in the PLL circuit can be obtained from the output terminal. Based on the voltage output from this output terminal, the oscillation frequency of the above-described oscillator circuit can be obtained. For this reason, the oscillation frequency of the above-described oscillator circuit can be obtained without the use of a frequency counter, so that the size of the apparatus can be reduced. Thus, because a frequency counter and a highly stable oscillator source are not used, the measuring apparatus can be manufactured at a low cost.

Since a measurement is a voltage, a change in frequency in a short period of time can be obtained by monitoring a change in this voltage.

Furthermore, an apparatus that is resistive to a change in temperature can easily be produced by matching the temperature characteristics between the above-described oscillator and the voltage-controlled oscillator.

Furthermore, an exciting electrode is formed of a sensitive membrane on one surface or both surfaces of the piezoelectric vibrating reed, and thereby this measuring apparatus can perform measurement both in liquid and air.

DETAILED DESCRIPTION OF THE PREFERRED EMBODIMENTS

Embodiments of a measuring method, a measurement-signal output circuit, and a measuring apparatus according to the present invention will now be described with reference to the attached drawings.

Figure 1:
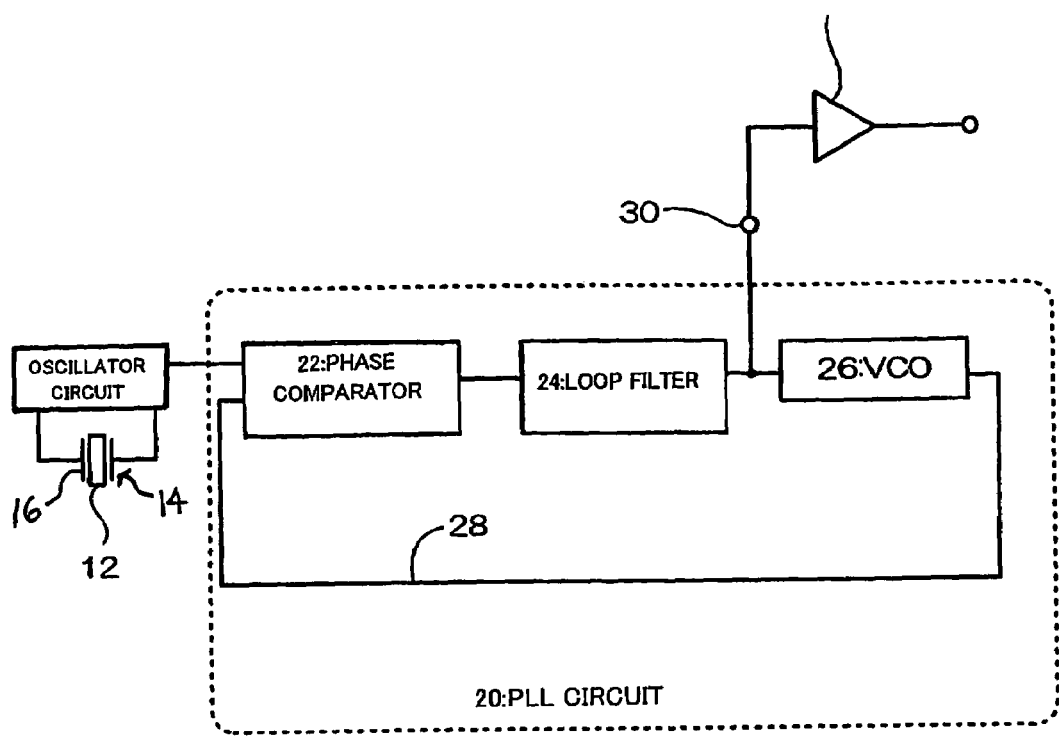
FIG. 1 is a block diagram of a measurement-signal output circuit according to the present embodiment.

FIG. 1 is a block diagram of a measuring apparatus according to the present embodiment. This measuring apparatus includes an oscillator circuit 10 which oscillates a mass-measuring vibrating reed and a measurement-signal output circuit which outputs a signal for detecting the oscillation frequency of the oscillator circuit which oscillates the above-described mass-measuring piezoelectric vibrating reed.

The mass-measuring vibrating reed (hereinafter, referred to as the piezoelectric vibrating reed 12) includes exciting electrodes 14 formed on both surfaces of the piezoelectric material, and has a sensitive membrane 16 applied to the exciting electrode 14 on one surface or sensitive membranes 16 applied to the exciting electrodes 14 on both surfaces. Here, the piezoelectric vibrating reed 12 having the sensitive membrane 16 applied to the exciting electrode 14 on one surface is used in liquid or air, whereas the piezoelectric vibrating reed 12 having the sensitive membranes 16 applied to the exciting electrodes 14 on both surfaces is used in air. Furthermore, the piezoelectric vibrating reed 12 is made of piezoelectric material such as a quartz vibrating reed. The oscillator circuit 10 which oscillates the piezoelectric vibrating reed 12 includes means (not shown) for outputting the oscillation frequency of the piezoelectric vibrating reed 12 to a phase comparator 22 of the measurement-signal output circuit as an input signal.

The measurement-signal output circuit for detecting the oscillation frequency of the mass-measuring vibrating reed includes a phase lock loop circuit 20 (hereinafter, referred to as a PLL circuit), which includes the phase comparator 22, a loop filter 24, and a VCO 26. The input end of the phase comparator 22 is connected to the output ends of the above-described oscillator circuit 10 and the VCO 26. The output end of this phase comparator 22 is connected to the input end of the loop filter 24, and the output end of the loop filter 24 is connected to the input end of the VCO 26. Furthermore, a feedback loop 28 is provided which feeds back the signal output from the VCO 26 to the phase comparator 22. The PLL circuit 20 is a closed circuit as a whole. In addition, the PLL circuit 20 is provided with an output terminal 30 which outputs the voltage output from the loop filter 24, and a buffer circuit 32 is connected to this output terminal 30.

The phase comparator 22 obtains the phase difference between the output signal output from the VCO 26 and the input signal from the oscillator circuit 10 outputting the oscillation frequency of the piezoelectric vibrating reed 12, and then outputs a deviation signal according to this phase difference to the loop filter 24. This loop filter 24 eliminates high-frequency components and noise of the above-described deviation signal, and outputs a smoothed DC voltage to the VCO 26. The VCO 26 outputs a frequency based on the above-described smoothed voltage to the phase comparator as an output signal. Here, the VCO 26 is oscillatable within a frequency range necessary for measurement including the oscillation frequency of the above-described piezoelectric vibrating reed 12.

In the above-described measuring apparatus provided with the measurement-signal output circuit for detecting the oscillation frequency of the mass-measuring vibrating reed, a method for measuring mass based on a change in oscillation frequency of the mass-measuring piezoelectric vibrating reed 12 is described below.

Figure 2:
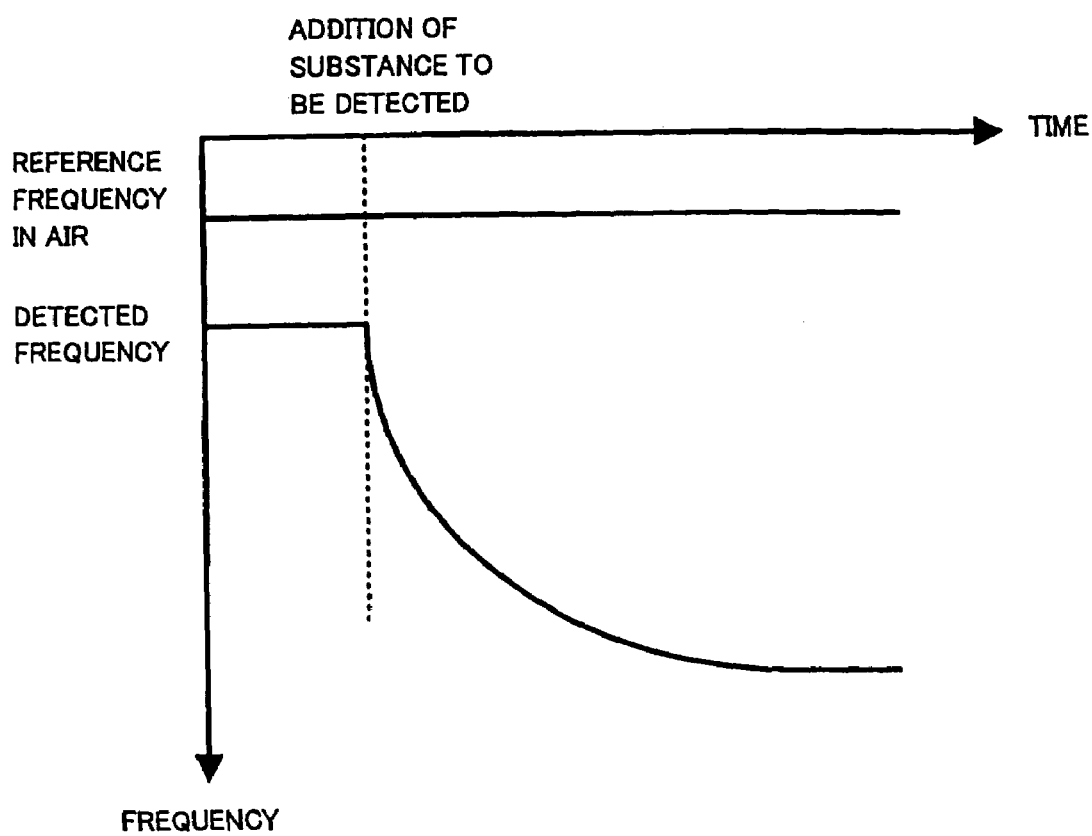
FIG. 2 shows a frequency detected in an oscillator circuit.

FIG. 2 shows a change in oscillation frequency of the piezoelectric vibrating reed 12 placed in a solvent when a substance to be detected is put into the solvent. First, the piezoelectric vibrating reed 12 functioning as a measuring sensor is placed in the solvent, and then the piezoelectric vibrating reed 12 is oscillated by the oscillator circuit 10. At this time, the oscillation frequency of the piezoelectric vibrating reed 12 becomes lower than the reference frequency in air. Next, the piezoelectric vibrating reed 12 is oscillated until stabilized, and then a substance to be detected is put into the above-described solvent in which the piezoelectric vibrating reed 12 is disposed. This substance to be detected diffuses in the solvent, and partly sticks to the above-described exciting electrode of the piezoelectric vibrating reed 12. At this time, the oscillation frequency of the piezoelectric vibrating reed 12 decreases because it has absorbed the above-described substance to be detected, and the oscillation frequency becomes lower as more of the substance is absorbed.

The oscillation frequency of the piezoelectric vibrating reed 12 at this time is input to the phase comparator 22 of the PLL circuit 20 via the oscillator circuit 10 as an input signal. Also, the output signal of the VCO 26 is input to the phase comparator 22. Then, the phase of the above-described input signal is compared with the phase of the above-described output signal, and a deviation signal according to this phase difference is output to the loop filter 24. In the loop filter 24, high-frequency components and noise of the above-described deviation signal are eliminated, and the deviation-signal is then output to the VCO 26 as a smoothed DC voltage. The VCO 26 oscillates based on the above-described DC voltage, and outputs a frequency which is voltage-controlled such that the phase difference from the above-described input signal becomes small. This output signal is fed back to the phase comparator 22 via the feedback loop 28.

In addition, a part of the above-described DC voltage output from the loop filter 24 is added to the output terminal 30 disposed on the output end of the loop filter 24. The PLL circuit 20 is a circuit which operates so as to phase-synchronize with the above-described input signal, and hence the above-described input signal correlates with the above-described deviation signal. Thus, the amount of change in voltage output from the output terminal 30 can be converted to the amount of change in oscillation frequency of the piezoelectric vibrating reed 12 by measuring and integrating the change in voltage. For this reason, a change in oscillation frequency resulting from the substance to be detected that sticks to the above-described piezoelectric vibrating reed 12 can be detected by measuring the above-described DC voltage output from the loop filter 24 of the phase lock loop circuit 20 at the above-described output terminal 30. Thus, for example, density detection of the above-described solution can be obtained when converted to a frequency from the amount of change in voltage output from the output terminal 30. Here, the buffer circuit 32 is connected to the output terminal 30, so that a change in frequency of the piezoelectric vibrating reed 12 can be obtained by measuring the voltage output from this buffer circuit 32 with a voltmeter, multimeter, or the like.

According to this embodiment, an oscillation frequency which changes due to the substance to be detected sticking to the piezoelectric vibrating reed 12 is phase-synchronized by the PLL circuit 20, and hence the input signal from the oscillator circuit 10 to the phase comparator 22 correlates with a smoothed DC voltage output from the loop filter 24. Therefore, a change in oscillation frequency of the piezoelectric vibrating reed 12 can be read by reading the amount of change in the above-described DC voltage output from the loop filter 24. A voltage output from the above-described loop filter 24 can be read out with a voltmeter, a multimeter, or the like, and hence it is not necessary to use a frequency counter. This enables the measuring apparatus for the mass-measuring vibrating reed to be made inexpensively and compactly.

Furthermore, in order to increase the sensitivity when a substance to be detected sticks to the piezoelectric vibrating reed 12, the reference frequency of the piezoelectric vibrating reed 12 is increased. For this purpose, however, the circuit of the measuring apparatus for the mass-measuring vibrating reed needs to handle a high-frequency signal. In the handling of a high-frequency signal in this embodiment, only the PLL circuit 20 handles a high-frequency signal, and therefore only the PLL circuit 20 needs a high-frequency countermeasure. That is, the buffer circuit 32 and the subsequent measuring devices do not need a high-frequency countermeasure. This increases the resistance to external electric fields and induction. For this reason, the size of the measuring apparatus for the mass-measuring vibrating reed can be reduced. That is, unlike the known art, impedance matching between the frequency counter as a measuring device and the oscillator circuit is not necessary. Furthermore, the circuit which handles a low-frequency signal does not need a high-frequency countermeasure. This enables the measuring apparatus for the mass-measuring vibrating reed to be produced at a low cost. Furthermore, the SN ratio is not degraded compared with a case where the entire measuring apparatus handles a high-frequency signal.

Figure 4:
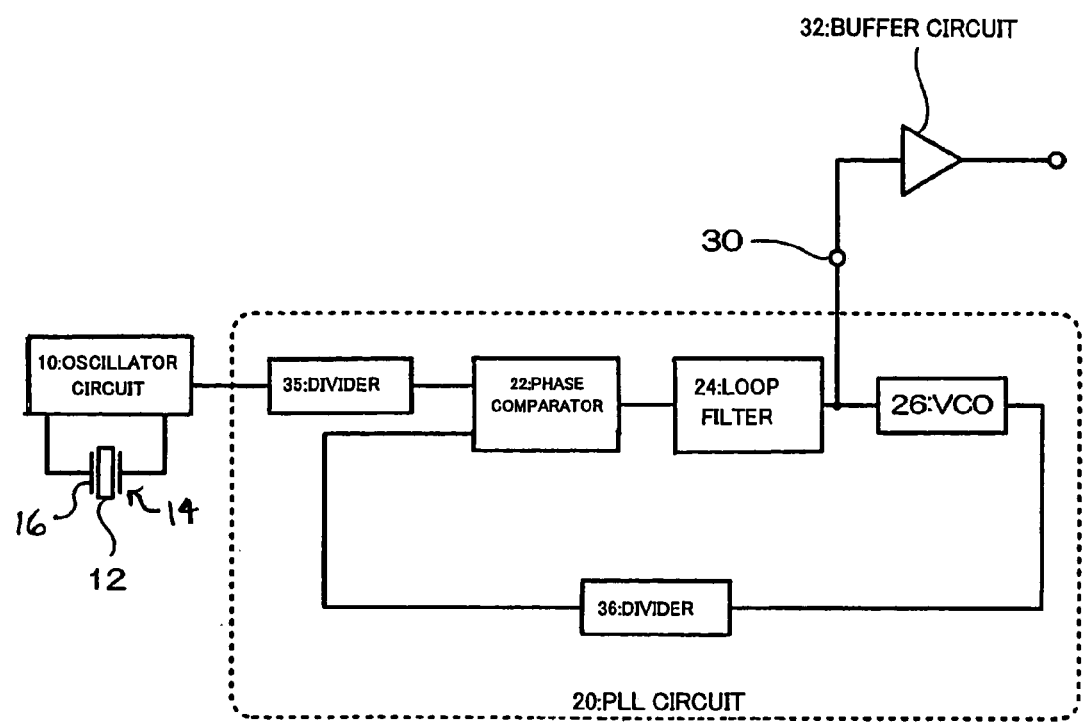
FIG. 4 is an illustration of a measurement-signal output circuit including a frequency divider according to the present embodiment.

Furthermore, as shown in FIG. 4, in order to increase the sensitivity, the reference frequency of the piezoelectric vibrating reed 12 is increased and this frequency is then divided into a lower frequency, which is then input to the PLL circuit 20. The oscillator circuit 10 and the phase comparator 22 are connected via a frequency divider 35 disposed therebetween. The VCO 26 and the phase comparator 22 are connected via a frequency divider 36 disposed therebetween.

The frequency output by the oscillator circuit 10 is divided by the frequency divider 35 to produce a lower frequency, which is then input to the phase comparator 22. Also, the frequency output by the VCO 26 is divided by the frequency divider 36 to produce a lower frequency, which is then input to the phase comparator 22. Even though the frequency of the oscillator circuit 10 is high, the operating frequency of the PLL circuit 20 can be decreased by adjusting the division ratio between the frequency divider 35 and the frequency divider 36, and thereby a compact and inexpensive apparatus which is also resistive to high-frequency noise can be realized.

In addition, according to this embodiment, a rapid frequency change within the range band-limited by the loop filter 24 of the PLL circuit 20 can be detected, and therefore a frequency change occurring in a very short period of time, for example, 0.1 s can be measured.

Furthermore, since the PLL circuit 20 including the oscillator circuit 10 is a small circuit, signals output from the relevant circuit have a low-frequency-band voltage. Hence, it is not necessary to take into consideration, for example, impedance matching for a connection between the relevant circuit and a voltmeter, a multimeter, or the like connected to this circuit. This enables the distance from the relevant circuit to the voltmeter, the multimeter, or the like to be freely set. Therefore, the relevant circuit can be more flexibly arranged and becomes more convenient.

Furthermore, frequency jitter occurring in the oscillator circuit 10 can easily be eliminated by adjusting the loop filter characteristics of the loop filter 24 and the VCO 26, and thereby the measurement SN ratio is enhanced.

This embodiment has been described where the oscillator for phase-synchronization in the PLL circuit 20 is the VCO 26. However, a voltage-controlled crystal oscillator or a voltage-controlled elastic surface wave oscillator can also be used to achieve more stable phase-synchronization of the PLL circuit 20.

In addition, the oscillator circuit 10 and the VCO 26 can be provided with a temperature sensor and a temperature-compensating circuit to correct for temperature characteristics between the oscillator circuit 10 and the VCO 26. Furthermore, changes in frequency of the oscillator circuit 10 and the VCO 26 due to a change in ambient temperature become identical to each other by matching the temperature characteristics of the oscillator circuit and the VCD, and hence the loop filter output of the PLL circuit 20 does not change. For this reason, the oscillator circuit 10 and the VCO 26 are not affected by the ambient temperature, and therefore it is not necessary to install the detection circuit in a temperature-controlled environment.

Figure 3:
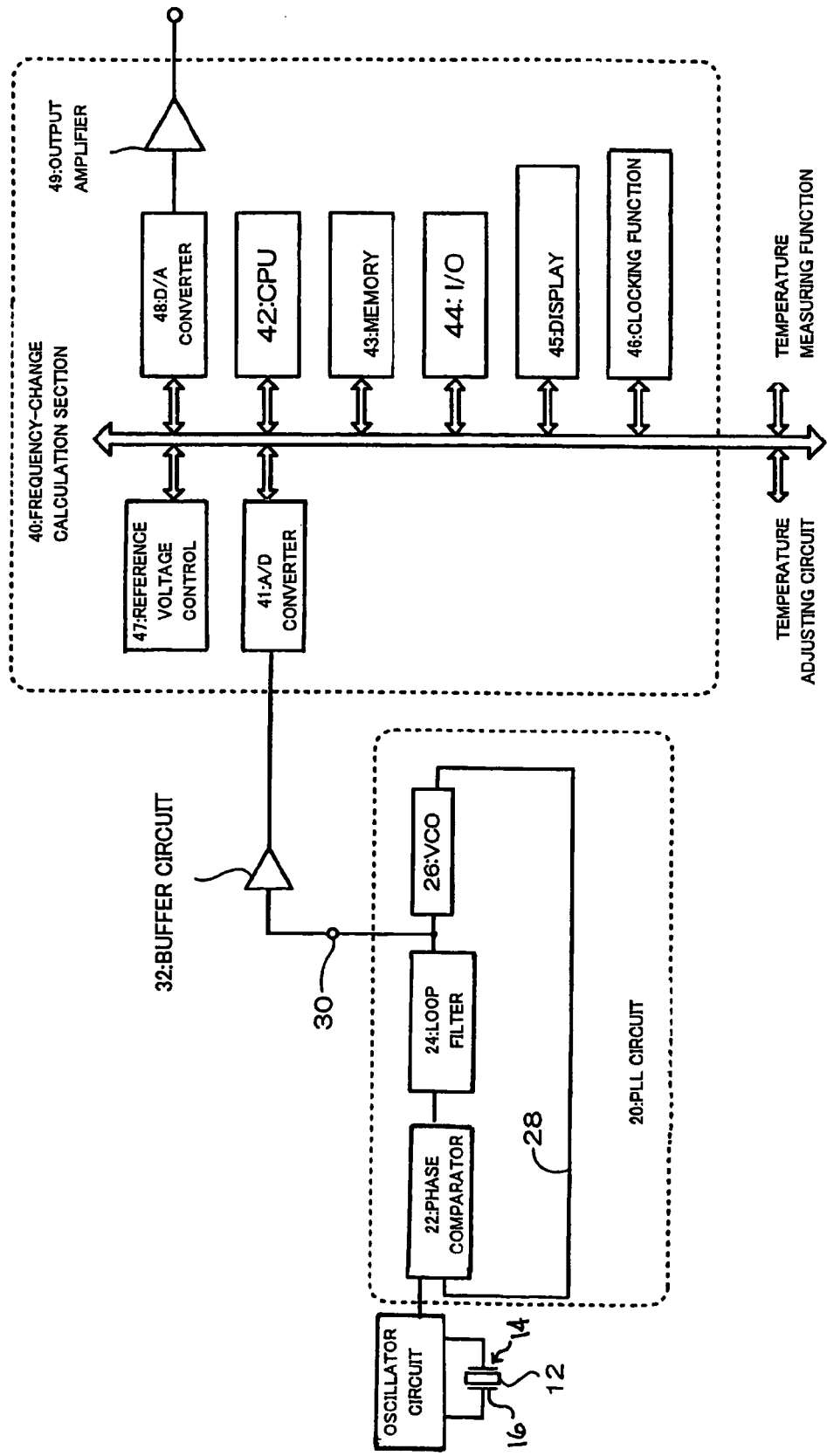
FIG. 3 is a block diagram of a measuring apparatus.

Furthermore, the frequency-change calculation section 40 can be connected to the output terminal 30 of the PLL circuit 20. A block diagram of this structure is shown in FIG. 3. This frequency-change calculation section 40 includes an A/D converter 41 which converts the output signal of the buffer circuit 32 from analog to digital, a Central Processing Unit (CPU) 42 which calculates the signal converted to digital, a memory 43, an input/output (I/O) device 44, a display 45, a clocking function 46, and a reference voltage control 47 for a reference voltage of the frequency-change calculation section 40. The frequency-change calculation section 40 further includes a D/A converter 48 which converts the calculated output signal, from digital to analog and an output amplifier 49 which amplifies this signal.

With this structure, the voltage signal output from the buffer circuit 32 is converted to a digital signal by the A/D converter 41 and then calculated, and this calculation result is displayed on the display 45, stored in the memory 43, and can be input/output to, for example, another device via the I/O 44. Furthermore, this calculation result can be converted to an analog signal by the D/A converter 48, so that the analog signal is output via the output amplifier 49. Because of this, an output of the buffer circuit 32, which is a voltage, can easily be subjected to A/D conversion, and therefore an integrated system for calculating measurement results can easily be constructed. This provides an inexpensive high-accuracy measuring apparatus with high time resolution.

In addition, the measuring method and the measuring apparatus for the mass-measuring vibrating reed according to this embodiment can be applied to, for example, a viscometer/densimeter, a moisture sensor, an odor sensor, and an ion sensor. First, the measurement principle for application as a viscometer/densimeter is described.

An AT-cut piezoelectric vibrating reed performs thickness-shear oscillation along its surface. When this AT-cut piezoelectric vibrating reed is placed in a liquid and then oscillated, shear stress occurs in the liquid. Because of this, from Newton's equation of viscosity and the equation of vibration of a quartz vibrator, the following expression representing the amount of change in frequency according to the viscosity of the liquid is derived.

$$\Delta F = -F^{\frac{3}{2}} \cdot \left(\frac{\eta \rho_L}{\pi \mu \rho}\right)^{\frac{1}{2}}$$

In the expression described above, $\Delta F$ is the amount of change in frequency of the piezoelectric vibrating reed, F is the frequency of the piezoelectric vibrating reed, $\eta$ is the viscosity of the liquid, $\rho_L$ is the density of the liquid, and $\mu$ is the modulus of elasticity of the piezoelectric material. According to the above-described expression, if one of the viscosity $\eta$ of the liquid and the density $\rho_L$ of the liquid is made constant, the amount of change in resonant frequency exhibits a one-to-one correspondence with the other. Therefore, a change in viscosity of the liquid or a change in density of the liquid can be obtained by measuring the amount of change in resonant frequency.

For application as an odor sensor, a sensitive membrane for selectively absorbing an odorant is formed on the surface of the piezoelectric vibrating reed. For application as a moisture sensor, an absorbing film is formed on the electrode of the piezoelectric vibrating reed. For application as an ion sensor, a sample solution is brought into contact with one electrode of the piezoelectric vibrating reed to make the electrode a work electrode, and is then subjected to electrodeposition with an electric field voltage for a certain period of time by using an electrolysis cell having a silver-silver chloride electrode or platinum wire as a counter electrode. Ions in the sample solution can be quantitatively analyzed from the amount of change in frequency of the piezoelectric vibrating reed arising from the above-described processing.

The invention claimed is:

1. A method for measuring mass from a change in oscillation frequency of a mass-measuring piezoelectric vibrating reed, the method comprising:

oscillating the piezoelectric vibrating reed with an oscillator circuit;

generating an output signal from the oscillator circuit that indicates an oscillating frequency of the vibrating reed;

dividing the output signal with a frequency divider to decrease a frequency of the output signal:

inputting THE DIVIDED OUTPUT signal from the oscillator circuit and an output signal from a voltage-controlled oscillator to a phase comparator of a phase lock loop circuit; and determining the oscillation frequency of the piezoelectric vibrating reed based on an output of a loop filter in the phase lock loop circuit.

2. The method of claim 1 further comprising dividing the output signal from the voltage-controlled oscillator with a second frequency divider.

3. The method of claim 1 further comprising determining a mass of a SUBSTANCE IN liquid based on the oscillation frequency.

4. A measurement-signal output circuit for outputting a signal for detecting an oscillation frequency of an oscillator circuit which oscillates a mass-measuring piezoelectric vibrating reed, the measurement-signal output circuit comprising:

a piezoelectric vibrating reed;

an oscillator circuit that oscillates the vibrating reed and outputs a signal indicative of the oscillating frequency of the vibrating reed;

a frequency divider that lowers a frequency of the signal;

a voltage-controlled oscillator oscillatable at an oscillation frequency of the piezoelectric vibrating reed;

a phase detector which obtains the difference in phase between an output signal from the voltage-controlled oscillator and the output signal from the FREQUENCY DIVIDER; and a loop filter having an output end connected to the voltage-controlled oscillator and an output terminal and outputting a voltage according to the difference in phase obtained by the phase detector.

5. The measurement-signal output circuit according to claim 4, wherein the piezoelectric vibrating reed has a sensitive membrane on an exciting electrode on one surface thereof that is in contact with liquid.

6. The measurement-signal output circuit according to claim 4, wherein the piezoelectric vibrating reed has a sensitive membrane on an exciting electrode on at least one of two surfaces thereof that is in contact with air.

7. The measurement-signal output circuit according to claim 4 further comprising a second frequency divider that lowers a frequency of the output signal from the voltage-controlled oscillator.

\* \* \* \* \*